United States Patent [19]
Moore

[11] Patent Number: 5,348,981
[45] Date of Patent: Sep. 20, 1994

[54] ANTIHERPETIC TREATMENT

[76] Inventor: Lillie B. T. Moore, 515 London House Rd., Montgomery, Ala. 36110

[21] Appl. No.: 125,242

[22] Filed: Sep. 23, 1993

[51] Int. Cl.$^5$ .............................................. A61K 47/00
[52] U.S. Cl. .................................. 514/788; 514/934; 424/713
[58] Field of Search ..................... 424/7; 514/788, 934

[56] References Cited

PUBLICATIONS

Merck Index 10th Ed. 1983, #'s 4347,212,211,1791,1792.
Bernand 78CA:140407y 1973.
Hodosh 107CA:283788f 1987.
Wagner 113CA65270j 1990.

Primary Examiner—Marianne M. Cintins
Assistant Examiner—Russell Travers

[57] ABSTRACT

All other products on the market only treat the herpes virus infection and help to ease the discomfort. The other products will not keep the virus from recurrening. Salphurbon Lotion was designed as a means to detroy the herpes virus, cure the infection, and prevent the virus from recurring in treated areas. Salphurbon Lotion is a medication designed to destroy the Herpes Type I and Type II virus. Salphurbon Lotion not only helps to eliminate the discomforts associated with the Herpes virus; it will also cure the infected area, and prevent recurring infections.

14 Claims, No Drawings

ANTIHERPETIC TREATMENT

FIELD

This invention relates to medication, specically a medication to cure Herpes Type I, Herpes Type II virus and the blisters and ulcerations associated with the virus.

SUMMARY

Salphurbon Lotion is a medication in lotion form which is used as a means to destroy the herpes virus, to cure the infection and to prevent the recurrence of the infection. Salphurbon Lotion consists of sulfur and charcoal mixed to a smooth paste with acohol and glycerine and added to a solution of Potassium Nitrate disolved in water. Salphurbon Lotion prevents the growth of bacteria by absorbing the moisture from the infected area. The Potassium Nitrate in Salphurbon Lotion has a drying effect and will not let moisture build up in the infected area. Salphurbon Lotion destroys the herpes virus so the infection will not reccur in the treated area.

DETAILED DESCRIPTION: SALPHURBON LOTION 100 grams Potassium Nitrate
15 grams Sulfur
12 grams U.S.P. Charcoal
300 ML Water Note: For a stronger solution Use 200 ML water.

Mix Potassium Nitrate with water at 100° F. degrees and stir until all Potassium Nitrate is disolved m water. Set liquid Potassium Nitrate solution aside. Ground sulphur into a fine power and disolve in 4 ML alcohol. Add 3 ML glycerine to sulphur and alcohol mixture stirring until a smooth paste is formed. Mix charcoal with 3 ML of glycerine and blend until completely blended, then add to sulphur mixture. Mix sulphur and charcoal mixture together and stir until a smooth paste is formed. Pour 50 ML of the liquid Potassium Nitrate solution into the mixture of sulphur and charcoal and stir until solution forms a creamy texture.

Salphurbon can be used as a lotion or added to an ointment base.

Salphurbon Lotion is a mild solution used to cure the Herpes Type I and Type II infections. The Salphurbon solution kills the Herpes virus heals the infections and prevents recurrence in the treated area. Wash affected area with warm water and apply Salphurbon Lotion. Apply Salphurbon Lotion to affected area 2 to three times per day. Lotion can be applied to areas on the vaginal wall. Discontinue sexual activity until infection heals.

Note: To make an ointment add solution to an ointment base.

I claim:

1. A method of treating herpetic lesions in a patient in need of such treatment comprising topically administering a composition consisting essentially of about 39% by weight Potassium nitrate, about 34.5% by weight sulfur, about 27.5% by weight carbon black in an aqueous carrier and optionally containing formulating agents at about 4% by weight.

2. The method of claim 1 wherein ethanol is employed at about 4% by weight and glycerin is employed at about 4% by weight as the formulating agents.

3. The method of claim 2 wherein the composition is applied in an ointment base.

4. The method of claim 1 wherein the treatment is administered to the affected area 2 times per day.

5. The method of claim 1 wherein the treatment is administered to the affected area 3 times per day.

6. The method of claim 1 wherein the etiological agent is herpes simplex type II.

7. The method of claim 1 wherein the etiological agent is herpes simplex type I.

8. A method of treating herpetic lesions ina patient in need of such treatment comprising topically administering a composition consisting essentially of about 48% by weight Potassium nitrate, about 29% by weight sulfur, about 23% by weight carbon black in an aqueous carrier and optionally containing formulating agents at about 4% by weight.

9. The method of claim 8 wherein ethanol is employed at about 4% by weight and glycerin is employed at about 4% by weight as the formulating agents.

10. The method of claim 9 wherein the composition is applied in an ointment base.

11. The method of claim 8 wherein the treatment is administered to the affected area 2 times per day.

12. The method of claim 8 wherein the treatment is administered to the affected area 3 times per day.

13. The method of claim 8 wherein the etiological agent is herpes simplex type II.

14. The method of claim 8 wherein the etiological agent is herpes simplex type I.

* * * * *